US006603548B2

(12) United States Patent
Church et al.

(10) Patent No.: US 6,603,548 B2
(45) Date of Patent: Aug. 5, 2003

(54) BIOSENSOR

(75) Inventors: Kenneth H. Church, Stillwater, OK (US); Robert M. Taylor, Perkins, OK (US)

(73) Assignee: Sciperio, Inc., Stillwater, OK (US)

( * ) Notice: Subject to any disclaimer, the term of this patent is extended or adjusted under 35 U.S.C. 154(b) by 28 days.

(21) Appl. No.: 09/727,691

(22) Filed: Dec. 4, 2000

(65) Prior Publication Data
US 2001/0028032 A1 Oct. 11, 2001

Related U.S. Application Data
(60) Provisional application No. 60/168,637, filed on Dec. 3, 1999.

(51) Int. Cl.[7] .................................................. G01J 3/28
(52) U.S. Cl. ...................................................... 356/326
(58) Field of Search ................................. 356/318, 317, 356/417, 326; 250/456.1, 459.1, 461.1, 461.2

(56) References Cited

U.S. PATENT DOCUMENTS

| 5,192,510 | A | * | 3/1993 | Zoha et al. ................. 356/244 |
| 5,300,423 | A | * | 4/1994 | Zoha et al. ................. 356/136 |
| 5,814,565 | A | * | 9/1998 | Reichert et al. .............. 385/12 |
| 5,818,582 | A | * | 10/1998 | Fernandez et al. ........ 250/458.1 |
| 5,961,924 | A | * | 10/1999 | Reichert et al. .............. 385/12 |
| 6,346,376 | B1 | * | 2/2002 | Sigrist et al. ................ 356/128 |
| 6,350,413 | B1 | * | 2/2002 | Reichert et al. .............. 385/12 |
| 2001/0028032 | A1 | * | 10/2001 | Church et al. ......... 250/227.14 |

* cited by examiner

Primary Examiner—Thien M. Le
(74) Attorney, Agent, or Firm—Needle & Rosenberg, P.C.

(57) ABSTRACT

A compact integrated biosensor has an integrated light source and integrated optical detectors made with gratings, dielectric coating, or prism for specific wavelength selection to define signatures that identify elements, biohazardous materials, environmentally hazardous materials, biological substance or any chemical substance on the sample holders. A micropump draws gas, ambient fluids and samples to the sample holders. Electrical signals are provided from the optical detectors on output lines to the microprocessor. A device connected to the microprocessor compares characteristic responses to actual signal parameters. An output indicates the presence (or absence) of particular biological, chemical or environmentally hazardous material. A battery, fuel cell or solar cell operated power supply provides electrical energy to the integrated light source and optical detectors. An ambient detector may provide a sample and hold memory for later releasing qualitative and quantitative information concerning the biosensor's environment and environmental history. Output of the biosensor may be continuous, periodical or on demand, or connected to a read-out device. The biosensor is usable as a badge by personnel or is attached to vehicles or mobile or stationary equipment, or to remote collection vehicles such as drones.

30 Claims, 2 Drawing Sheets

BIOSENSOR

This application claims the benefit of U.S. Provisional Application No. 60/168,637 filed Dec. 3, 1999.

BACKGROUND OF THE INVENTION

Needs exist for new and improved biosensors.

SUMMARY OF THE INVENTION

The invention provides compact integrated sensors.

The biosensor has an integrated light source and integrated optical detectors. The integrated optical waveguides are made with gratings, dielectric coating, or prisms for specific wavelength selection. That allows peaks in the optical detector array to define signatures that identify elements, biohazardous materials, environmentally hazardous materials, biological substance or any chemical substance on the sample holders.

Each sample holder has several options: One sample holder is made using etched channels or canals in the substrate. Optically transparent material in the holder acts as a waveguide for light, the support structure for a selective coating, the collection matrix, or a combination of these things. One holder has a selective coating on it. Another holder just contains the sample of interest.

A micropump draws gas, ambient fluids and samples to the sample holders. Electrical signals are provided from the optical detectors on output lines to the microprocessor. A device connected to the microprocessor compares characteristic responses to actual signal parameters. An output indicates the presence (or absence) of particular biological, chemical or environmentally hazardous material. Several distinct sensors may be used together for sampling different biological, chemical or environmentally hazardous material.

A battery, fuel cell or solar cell operated power supply provides electrical energy to the light source, the optical detectors micropump and the microprocessor.

A device connected to the processor may provide a sample and hold memory for later releasing qualitative and quantitative information concerning the biosensor's environment and environmental history. Output of the biosensor may be continuous, periodical or on demand, or connected to a read-out device.

The biosensor may be used as a badge by personnel or is attached to vehicles or mobile or stationary equipment, or to remote collection vehicles such as drones.

It is within the scope of this invention to integrate the micropump, microprocessor and power sources.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
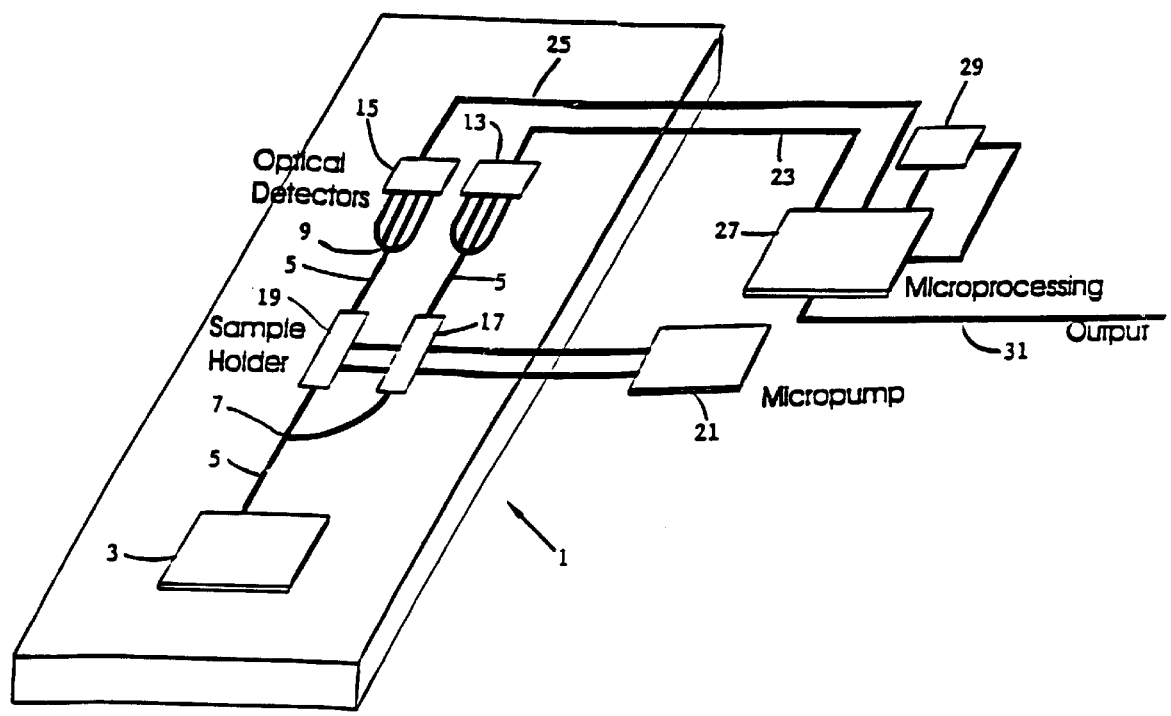
FIG. 1 is a schematic representation of a biosensor.

The biosensor 1 shown in FIG. 1 has an integrated light source 3. The integrated optical waveguides 5 are made with gratings, dielectric coatings, or prisms 7 and 9 for specific wavelength selection 11. That allows peaks in the optical detectors 13, 15 to define signatures that identify chemical elements, biohazardous materials, environmentally hazardous materials, or other biological/chemical substance on the sample holders 17, 19. Each sample holder has several options: One sample holder is made using etched channels or canals in the substrate. Optically transparent material in the holder acts as a waveguide for light, the support structure for a selective coating, the collection matrix, or a combination of these things. In one example a holder has a selective coating on it. In another example a holder just contains the sample of interest.

Figure 2:
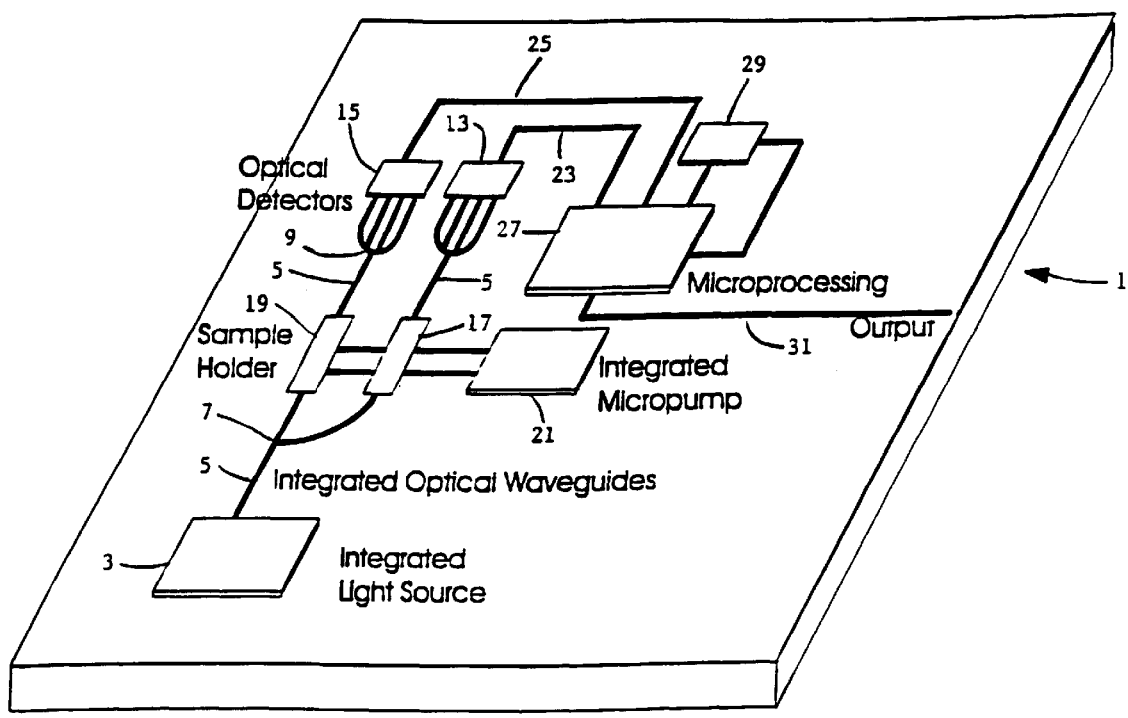
FIG. 2 is a schematic representation of a stand alone, integrated biosensor.

FIG. 2, shows a biosensor with an integrated micropump 21 draws ambient fluids and samples to the sample holders 17, 19. Electrical signals are provided from the optical detectors 13, 15 over output lines 23 and 25 to microprocessor 27. A device 29 connected to the microprocessor compares characteristic responses to actual signal parameters. An output 31 indicates the presence (or absence) of a particular biological, chemical or environmentally hazardous material. Several distinct sensors may be used together for sampling different biological, chemical or environmentally hazardous material.

An integrated battery, fuel cell or solar cell operated power supply provides electrical energy to the light source 3, the optical detectors 13, 15, micropump 21 and the microprocessor 27.

A device 29 connected to the processor may provide a sample and hold memory for later releasing qualitative and quantitative information concerning the biosensor's environment and environmental history. Output of the biosensor may be continuous, periodical or on demand, or connection to a read-out device. An on board memory may record times, types and extent of biohazards for later readout. Biosensor 1 may be operated using pumps, microprocessors, power sources, as described above.

The biosensor is used as a badge by personnel or is attached to vehicles or mobile or stationary equipment, or to renote collection vehicles such as drones. The biosensor samples fluids and records data on fluid quality and biohazards or may have real time connections between the output 31 and coupled alarms, alerts, recorders or telemetering devices.

The invention provides compact integrated sensors.

While the invention has been described with reference to specific embodiments, modifications and variations of the invention may be constructed without departing from the scope of the invention, which is defined in the following claims.

We claim:

1. Detection apparatus comprising at least one biosensor which includes at least one optical source, at least one sample holder for receiving substances, optical waveguides for transmitting light from the optical source to the sample holder, optical detectors for detecting the substances exposed to the sample holder and a microprocessor for receiving signals from the optical detectors and outputting data relative to the substances detected, wherein the optical waveguides further comprise gratings, dielectric coatings, or prisms for specific wavelength selection corresponding to substances to be detected.

2. The apparatus of claim 1, wherein at least one optical source, at least one sample holder, the optical waveguides and the optical detectors are integrated.

3. The apparatus of claim 1, wherein each sample holder comprises a substrate and etched channels on the substrate.

4. Detection apparatus comprising at least one biosensor which includes at least one optical source, at least one sample holder for receiving substances, optical waveguides for transmitting light from the optical source to the sample holder, optical detectors for detecting the substances exposed to the sample holder and a microprocessor for receiving signals from the optical detectors and outputting data relative to the substances detected, wherein each sample holder comprises an optically transparent material acting as a waveguide for the light.

5. The apparatus of claim 1, wherein the sample holder has a selective coating.

6. The apparatus of claim 1, wherein the optical detectors communicate with the optical waveguides for providing peaks to define signature corresponding to the specific wavelength for identifying substances detected.

7. The apparatus of claim 6, wherein the substances are selected from a group consisting of chemical elements, biohazardous materials, environmentally hazardous materials, biological and chemical substances.

8. The apparatus of claim 6, further comprising output lines connecting the optical detectors to the microprocessor for providing signals to the microprocessor.

9. The apparatus of claim 8, further comprising a comparator connected to the microprocessor for comparing characteristic responses to actual signal parameters.

10. The apparatus of claim 8, further comprising an output connected to the microprocessor for indicating presence or absence of a particular substance.

11. The apparatus of claim 1, further comprising plural biosensors for sampling different biological, chemical or environmentally hazardous material.

12. The apparatus of claim 1, further comprising an integrated micropump for drawing ambient fluids and samples to the sample holders.

13. The apparatus of claim 1, further comprising an integrated power source connected to the biosensor.

14. The apparatus of claim 13, wherein the power source is selected from the group consisting of battery, or fuel cell, or solar cell and power supply.

15. The apparatus of claim 1, further comprising an ambient sensor connected to the microprocessor having a memory device for recording and providing qualitative and quantitative information relating to ambient environmental history.

16. The apparatus of claim 1, wherein an output of the biosensor may be continuous, periodical or on demand, or connection to a read-out device.

17. The apparatus of claim 1, further comprising an on board memory device for recording times, types and extent of biohazards for later retrieval.

18. The apparatus of claim 1, wherein the biosensor is a badge attachable to personnel, vehicles, mobile equipment, stationary equipment, and to remote collection vehicles.

19. The apparatus of claim 1, wherein the biosensor comprises information on fluid or air samples and data on fluid quality and biohazards.

20. The apparatus of claim 1, further comprising alert devices connected in real time to the biosensor for alerting in response to samples detected.

21. A method for detection of substances with an integrated and compact biosensor comprising providing a sample on a sample holder, providing an integrated light source, connecting optical waveguides for providing signal from the light source to the sample holder, providing integrated optical detectors for receiving signals from the sample holder, connecting the biosensor to a microprocessor for computing signals received from the detector and outputting data relative to the sample detected, and selecting specific wavelengths with gratings on the optical detectors.

22. The method of claim 21, wherein the selection of specific wavelengths defines signatures identifying substances relative to the specific wavelengths of substances detected.

23. The method of claim 22, wherein the substances detected are selected from the group consisting of biohazardous materials, environmentally hazardous materials, biological substances, and chemical substances or combinations thereof.

24. The method of claim 22, further comprising supplying gas, ambient fluids and samples by an integrated micropump to the sample holder.

25. The method of claim 24, further comprising comparing characteristic responses to actual signal parameters with a comparator and outputting data indicating presence or absence of particular substances detected.

26. The method of claim 21, further comprising detecting different biological, chemical or environmentally hazardous material with plural biosensors used together.

27. The method of claim 22, further comprising providing an ambient sensor device for recording and retrieving data on quantitative information relative to environmental history.

28. The method of claim 22, wherein an output of the biosensor is provided continuously, periodically or on demand.

29. The method of claim 21, further comprising providing the biosensor as a badge attachable to personnel, vehicles, mobile equipment, stationary equipment, and remote collection vehicles.

30. A method for detection of substances with an integrated and compact biosensor comprising providing a sample on a sample holder, providing an integrated light source, connecting optical waveguides for providing signal from the light source to the sample holder, providing integrated optical detectors for receiving signals from the sample holder, and connecting the biosensor to a microprocessor for computing signals received from the detector and outputting data relative to the sample detected, wherein each sample holder comprises an optically transparent material acting as a waveguide for the light.

* * * * *